United States Patent [19]

Tabak

[11] Patent Number: 4,513,156
[45] Date of Patent: Apr. 23, 1985

[54] OLEFIN OLIGOMERIZATION USING EXTRACTED FEED FOR PRODUCTION OF HEAVY HYDROCARBONS

[75] Inventor: Samuel A. Tabak, Wenonah, N.J.

[73] Assignee: Mobil Oil Corporation, New York, N.Y.

[21] Appl. No.: 600,699

[22] Filed: Apr. 16, 1984

[51] Int. Cl.$^3$ .............................................. C07C 2/02
[52] U.S. Cl. .................................. 585/329; 585/517; 585/533
[58] Field of Search ......................... 585/329, 517, 533

[56] References Cited

U.S. PATENT DOCUMENTS

| | | | |
|---|---|---|---|
| 4,111,792 | 8/1978 | Caesar et al. | 585/251 |
| 4,213,847 | 7/1980 | Chen et al. | 208/111 |
| 4,260,841 | 4/1981 | Holland et al. | 585/319 |
| 4,433,185 | 2/1984 | Tabak | 585/312 |
| 4,444,988 | 4/1984 | Capsuto et al. | 585/415 |
| 4,456,779 | 6/1984 | Owen et al. | 585/415 |

OTHER PUBLICATIONS

M. E. Dry, "High Yield Quality Diesel from Fischer–Tropsch Process", Chem. SA, v. 10(2), pp. 286–287, 290, 1984.

*Primary Examiner*—Curtis R. Davis
*Attorney, Agent, or Firm*—A. J. McKillop; M. G. Gilman; L. G. Wise

[57] ABSTRACT

A process is disclosed for oligomerizing olefinic Fischer-Tropsch liquids to produce heavier hydrocarbons by converting olefinic feedstock containing oxygenated hydrocarbons over an acidic zeolite catalyst. The improvement comprises extracting oxygenates from the feedstock; converting the extracted feedstock in a primary stage distillate mode catalytic reactor system under low severity conditions at high pressure and moderate pressure; and recovering the oxygenates and light hydrocarbons from the primary stage for conversion in a secondary stage reactor system under high severity conditons at substantially higher temperature than the primary stage, thereby converting oxygenates and light hydrocarbons to heavier hydrocarbons.

10 Claims, 2 Drawing Figures

OLEFIN OLIGOMERIZATION USING EXTRACTED FEED FOR PRODUCTION OF HEAVY HYDROCARBONS

FIELD OF INVENTION

This invention relates to a continuous technique for converting olefin feedstock to heavier hydrocarbons, especially for the manufacture of distillate range hydrocarbon fuels. In particular it provides a system for operating an integrated two-stage MOGD type plant wherein an oligomerization catalyst, such as crystalline zeolite of the ZSM-5 type, is employed for converting olefinic feedstocks containing liquid alkenes and oxygenates at elevated temperature and pressure.

BACKGROUND OF THE INVENTION

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. Nos. 4,150,062 and 4,227,992 Garwood et al disclose the operating conditions for the Mobil Olefin to Gasoline Distillate (MOGD) process for selective conversion of $C_3+$ olefins.

The phenomena of shape-selective polymerization are discussed by Garwood in ACS Symposium Series No. 218, Intrazeolite Chemistry, "Conversion of $C_2$-$C_{10}$ to Higher Olefins over Synthetic Zeolite ZSM-5", 1983 American Chemical Society.

Typically, the process recycles cooled light hydrocarbons from a high-temperature, high-pressure separator downstream of the catalyst bed back into the reaction zone where additional olefins are converted to gasoline and distillate products. If the reaction of the olefins in converting them to distillate and gasoline is allowed to progress in the catalyst stream without any measures taken to prevent the accumulation of heat, the reaction becomes so exothermically accelerated as to result in high temperatures and the production of undesired products.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$-$C_6$ alkenes may be converted selectively; however, the distillate mode conditions do not convert a major fraction of ethylene due to low severity conditions. While propene, butene-1 and others may be converted to the extent of 50 to 95% in the distillate mode, only about 10 to 50% of the ethylene component will be consumed.

In the high severity or gasoline mode, ethylene and the other lower olefins are catalytically oligomerized at higher temperature and moderate pressure. Under these conditions ethylene conversion rate is greatly increased and lower olefin oligomerization is nearly complete to produce an olefinic gasoline comprising hexene, heptene, octene and other $C_6+$ hydrocarbons in good yield. To avoid excessive temperatures in the exothermic reactors, the lower olefinic feed may be diluted. In the distillate mode operation, olefinic gasoline may be recycled and further oligomerized, as disclosed in U.S. Pat. Nos. 4,211,640 (Garwood and Lee) and 4,433,185 (Tabak). The above cited publications are incorporated herein by reference.

One important source of olefinic feedstocks of interest for conversion to heavier fuel products is the intermediate olefin-rich light oil or naphtha obtained from Fischer-Tropsch conversion of synthesis gas. These synthol materials contain, in addition to olefins, a minor amount of coproduced oxygenated hydrocarbons. It has been found that these oxygenates can interfere with catalytic oligomerization of olefins, particularly under the low severity conditions employed for making distillate and heavier hydrocarbons. It is an object of this invention to overcome such catalytic deactivation by oxygenates, and to provide manufacturing methods and apparatus adapted to employ Fischer-Tropsch liquid feedstocks.

SUMMARY

A process has been discovered for converting olefins to heavier liquid hydrocarbons comprising contacting an olefinic liquid hydrocarbon feedstream containing oxygenated hydrocarbons with a polar solvent under liquid extraction conditions and recovering a polar extract phase containing the oxygenated hydrocarbons and an olefinic liquid raffinate stream substantially free of oxygenated hydrocarbons; contacting the olefinic liquid stream in a first catalyst reactor zone with oligomerization catalyst at elevated pressure and moderate temperature under conditions favorable for conversion of olefins to a first reactor effluent stream rich in distillate range hydrocarbons; flashing the distillate-rich stream and separating the first reactor effluent stream into a liquid product stream rich in distillate and a vapor stream containing lower hydrocarbons; separating oxygenated hydrocarbons from the polar extract phase; and contacting at least a portion of the vapor stream from the flashing step and recovered oxygenated hydrocarbons in a second catalyst reactor zone with oligomerization catalyst at moderate pressure and elevated temperature under conditions favorable for conversion of lower olefins and oxygenates to a second reactor effluent stream rich in heavier hydrocarbons. The process is particularly useful where the olefinic feedstream is rich in $C_3+$ mono-olefins and contains a minor amount of $C_2$-$C_6$ oxygenates. Advantageously the polar solvent consists essentially of water, and by-product water is recovered from at least one reactor zone and recycled as extraction solvent.

In order to maximize distillate production the first and second effluent streams may be fractionated to provide a gasoline-range hydrocarbon stream, and at least a portion of the gasoline stream is recycled to the first reactor zone.

THE DRAWINGS

FIG. 1 is a process flow sheet showing the major unit operations and hydrocarbon streams; and FIG. 2 is a graphic plot of operating temperature and stream time for comparative runs using two feedstocks.

DESCRIPTION OF THE PREFERRED EMBODIMENTS

Figure 1:
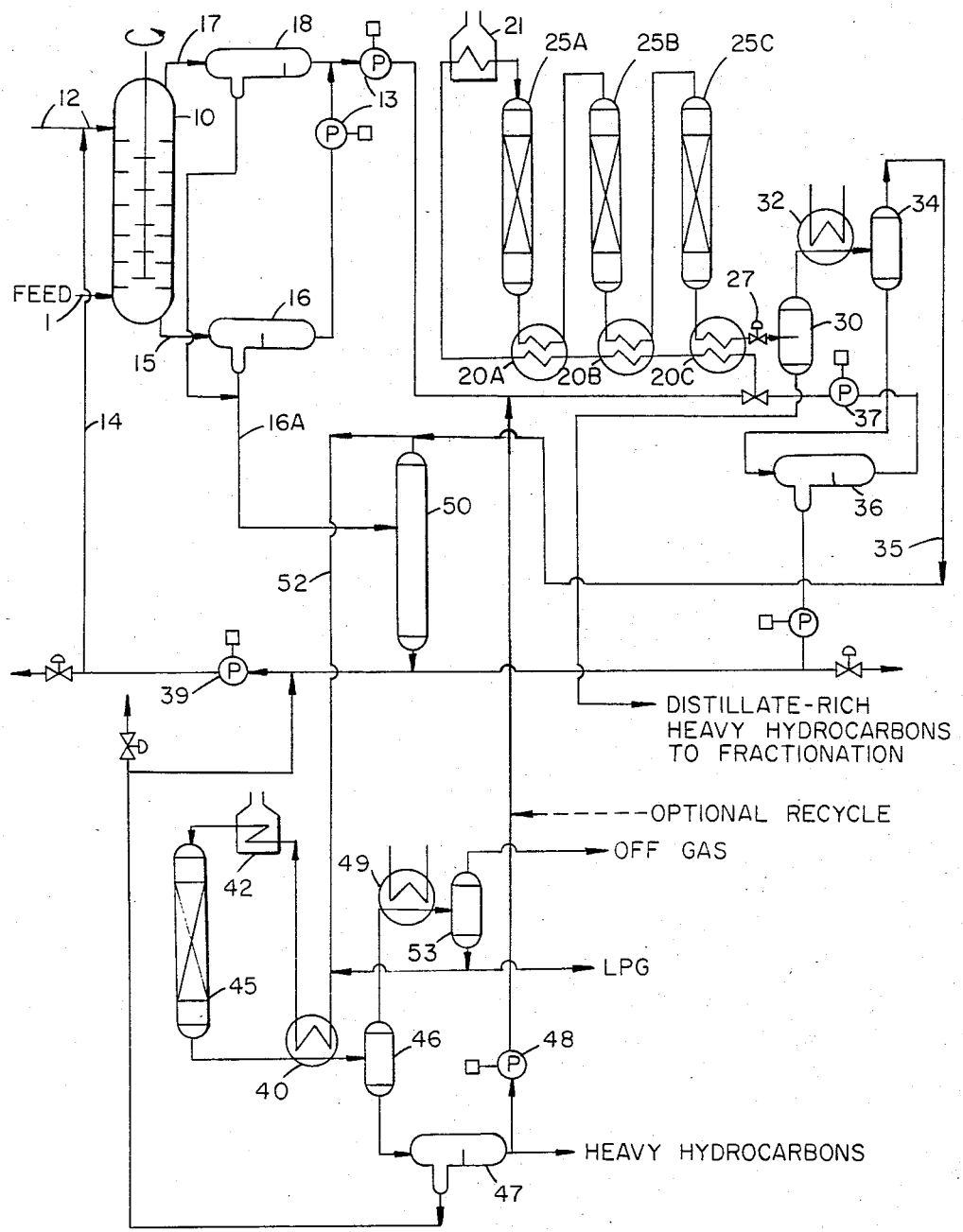

The oligomerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed is a HZSM-5 zeolite with alumina binder in the form of cylindrical extrudates of about 1–5 mm. Other pentasil catalysts which may be used in one or more reactor stages include a variety of medium pore ($\sim$5 to 9 Å) siliceous materials such as borosilicates, ferrosilicates, and/or aluminosilicates disclosed in U.S. Pat. Nos. 4,414,143 and 4,417,088, incorporated herein by reference.

The present invention is intended primarily for conversion of olefinic feedstocks containing a major amount of naphtha range aliphatic hydrocarbons in combination with a minor amount of oxygenated hydrocarbons. Typically, the feedstock is rich in volatile $C_3$–$C_{10}$ liquid mono-olefins; however, more volatile and heavier hydrocarbons in the $C_2$–$C_{12}$ range may be present. The process is particularly well adapted to oligomerizing $C_3$–$C_7$ olefins. Ethylene may be present to the extent it would be soluble in the liquid feedstock under process conditions.

Referring to the drawing, feedstock consisting essentially of Fischer-Tropsch naphtha fraction is introduced via feed conduit 1 to the bottom inlet of a continuous liquid-liquid extraction unit 10 wherein it is contacted in countercurrent flow operation with a polar solvent introduced via top solvent conduit 12 wherein makeup solvent (e.g., water) is combined with a recycle stream 14, which may consist essentially of recycled polar solvent with a minor amount of residual oxygenate. The extraction unit 10 depicted is a stirred multi-stage vertical extraction column adapted for contiuous operation at superatmospheric pressure (e.g., about 600 to 1500 kPa). It is understood that any suitable extraction equipment may be employed, including cocurrent, cross-current or separate stage contactors, wherein the liquid feedstock is intimately contacted with an immiscible solvent. This unit operation is described in *Kirk-Othmer Encyclopedia of Chemical Technology* (Third Ed.), 1980, pp. 672–721. The oxygenate extraction step can be carried out in any counter-current multistage design such as a simple packed column, rotating disk column, agitated column with baffles or mesh, or a series of single stage mixers and settlers.

The heavier solvent phase, rich in oxygenate solute, is recovered via bottom outlet 15 and may be further separated by decanting any hydrocarbon phase carryover in separator 16 to be combined wih the main naphtha raffinate stream 17 exiting the extraction column 10 via another decanting unit 18 before being pressurized by pumps 19. The extracted feedstock is then heated to reaction pressure by passing sequentially through reactor effluent heat exchangers 20C, B, A and furnace 21 prior to entering a series of fixed bed catalytic reactors 25A, B, C containing the oligomerization catalyst. These reactors are preferably operated in the distillate mode to maximize production of $C_{10}+$ aliphatics. The cooled effluent from the last reactor 25C is flashed by passing through pressure reduction valve 27 into a first high temperature separator drum 30, from which a heavy hydrocarbon product rich in $C_{10}$–$C_{20}$ distillate is recovered. Overhead vapor from separator 30 is cooled by heat exchanger 32 and condensate is passed from second low temperature separator 34 to a liquid decanting unit 36 for recovery of any byproduct water, which is recycled via conduit 38 and pump 39 to recycle line 14. The hydrocarbon phase from liquid decanting unit 36 is recycled via pump 37 for combining with feedstock to the first distillate mode reactor stage. Overhead vapor from the second separator 34 is passed via conduit 35 through heat exchanger 40 and furnace 42 to the second reactor stage 45, which is operated under high severity conversion conditions at elevated temperature and reduced pressure, as compared to the first stage. The increased temperature is sufficient to oligomerize unconverted light olefins from the first stage, even in the presence of water. The second stage effluent stream, rich in gasoline range hydrocarbons and other heavier hydrocarbons, is then cooled in exchanger 40 and passed to the recovery section. Condensed water may be recovered along with heavy liquid hydrocarbons from high temperature separator 46 and decanter 47. The gasoline-rich hydrocarbons may be recycled via pump 48 for combining with feedstock prior to the first stage. Overhead vapor from the secondary stage separator 46 may be further cooled by exchanger 49 to obtain an offgas stream and $C_3$–$C_4$ rich in LGP product, a portion of which may be recycled to the secondary stage as a heat sink or diluent. Distillate and/or gasoline range heavy hydrocarbons may be recovered and fractionated separately from each of the main stages.

Fractionation of the distillate rich first stage product and gasoline rich second stage product streams may be effected in any suitable manner, including the distillation technique disclosed in U.S. patent application Ser. No. 488,834, filed Apr. 26, 1983 (Owen et al), incorporated herein by reference. Optionally, a portion of the gasoline range hydrocarbons from fractionation may be combined with feedstock prior to the first stage.

The water phase recovered from the extraction unit 10 may be recovered and taken out of the system; however, it is preferred to recover oxygenates for conversion under high severity conditions in the secondary stage reactor. Advantageously, the oxygenate-rich extract is passed via conduit 49 to distillation tower 50 where the volatile organic compounds are stripped from the polar solvent. The overhead stream 52, which may contain water in addition to to oxygenates, is combined with light olefinic gas from conduit 35 prior to the secondary stage. In general, it is advantageous to minimize the quantity of water the overhead stream from tower 50. However, where oxygenated compounds are present which may boil close to the boiling point of water, carryover in conduit 52 may be as high as 5 parts water to 1 part oxygenates. Bottoms from tower 50 may be combined with byproduct water and recycled via pump 39 and conduit 14 to the extraction unit.

It is advantageous to have the water travel in a closed loop so that any hydrocarbons carried into the water phase during extraction do not need to be removed from the water. Excess water such as produced by oxygenate dehydration can be removed by any of several available purge lines. Also, since the second stage reactor 45 will dehydrate the oxygenates it will act to remove oxygenates from the extraction loop while purifying the water phase.

The extraction unit may be operated from 0° to 100° C., preferably at ambient temperature (20°-25° C.) and under pressure. While approximately equal amounts of water and feedstock are satisfactory, their ratios may be varied widely (e.g., 10:1 to 1:10 parts by volume). Fischer-Tropsch naphtha (i.e. synthol light oil) typically contains about 2 to 15 wt % oxygenates. In one example herein a $C_5$-$C_6$ olefinic feedstock is extracted in multiple stages to reduce the oxygenate content of the raffinate at substantially below 1 wt %.

In order to demonstrate the differences between unextracted feedstocks containing oxygenates and oxygenate-free olefinic feedstock comparative runs are made in a continuous process. Operating in the maximum distillate mode under low severity conditions at moderate temperature and high pressure, the runs are conducted for a period of seven days on stream, using a fixed bed of standard small crystal HZSM-5 extrudate catalyst having an acid activity ($\alpha$) of about 175 and containing 35% alumina binder. The process was operated at sufficient temperature to achieve essentially complete conversion of $C_5$-$C_6$ olefins. Feedstock composition and process results are tabulated below for each feedstock.

TABLE I $C_5$-$C_6$ OLEFIN FEEDSTOCK*
OXYGENATE-FREE

| DAYS ON STREAM | 1 | 2 | 3 | 4 | 5 | 6 | 7 |
|---|---|---|---|---|---|---|---|
| OPERATING CONDITIONS | | | | | | | |
| Ave. Reactor Temp., F. | 399 | 399 | 405 | 406 | 409 | 412 | 420 |
| Pressure, psig | 601 | 601 | 601 | 601 | 602 | 602 | 602 |
| LHSV (Total) | 1.0 | 1.0 | 1.0 | 1.0 | 1.0 | 1.0 | 1.0 |
| LHSV (Olefin) | 0.8 | 0.8 | 0.8 | 0.8 | 0.8 | 0.8 | 0.8 |
| TOTAL OLEFIN CONVERSION, WT % | 100.00 | 99.99 | 100.00 | 99.98 | 99.86 | 99.84 | 99.89 |
| 1-Pentene Conv., wt % | 100.00 | 99.98 | 99.99 | 99.97 | 99.73 | 99.69 | 99.79 |
| 1-Hexene Conv., wt % | 100.00 | 100.00 | 100.00 | 100.00 | 100.00 | 100.00 | 100.00 |
| PRODUCT YIELDS (On conv. olefin) | | | | | | | |
| $C_4^-$, wt % | 0.78 | 0.67 | 0.27 | 0.54 | 3.01 | 0.14 | 0.42 |
| $C_5$-330F Gasoline, wt % | 14.83 | 15.12 | 15.85 | 15.62 | 22.45 | 23.68 | 22.55 |
| 330F + Distillate, wt % | 84.39 | 84.21 | 83.88 | 83.84 | 74.53 | 76.18 | 77.03 |
| GASOLINE, API | 77.4 | 76.7 | 76.3 | 76.2 | 75.0 | 74.6 | 75.0 |
| 5 wt %, F | 87 | 89 | 89 | 90 | 97 | 106 | — |
| 50 wt %, F | 164 | 164 | 165 | 177 | 159 | 166 | — |
| 95 wt %, F | 336 | 339 | 344 | 324 | 337 | 356 | — |
| DISTILLATE, API | 45.5 | 46.5 | 46.5 | 47.0 | 50.5 | 50.2 | 49.9 |
| 5 wt %, F | 326 | 323 | 321 | 319 | 315 | 312 | 319 |
| 50 wt %, F | 505 | 492 | 488 | 482 | 385 | 384 | 398 |
| 95 wt %, F | 767 | 734 | 733 | 724 | 634 | 642 | 650 |
| TLP 50% PT, F | 405 | 387 | 390 | 385 | 345 | 345 | 347 |

| *FEED COMPONENTS | Weight % |
|---|---|
| 1-Pentene | 35.0 |
| 1-Hexene | 49.0 |
| N—Hexane | 16.0 |

TABLE II $C_5$-$C_6$ OLEFIN FEEDSTOCK*
WITH 2.5 WT % OXYGENATES

| DAYS ON STREAM | 1 | 2 | 3 | 4 | 5 | 6 | 7 |
|---|---|---|---|---|---|---|---|
| OPERATING CONDITIONS | | | | | | | |
| Ave. Reactor Temp., F. | 398 | 444 | 475 | 483 | 491 | 495 | 503 |
| Pressure, psig | 605 | 607 | 615 | 600 | 600 | 602 | 601 |
| LHSV (Total) | 1.0 | 1.0 | 0.9 | 1.0 | 1.0 | 1.0 | 1.0 |
| LHSV (Olefin) | 0.8 | 0.8 | 0.8 | 0.9 | 0.8 | 0.8 | 0.8 |
| TOTAL OLEFIN CONVERSION, WT % | 94.17 | 99.24 | 99.89 | 99.95 | 99.89 | 99.88 | 99.94 |
| 1-Pentene Conv., wt % | 92.56 | 98.82 | 99.77 | 99.90 | 99.77 | 99.74 | 99.87 |
| 1-Hexene Conv., wt % | 95.35 | 99.60 | 100.00 | 100.00 | 100.00 | 100.00 | 100.00 |
| PRODUCT YIELDS (On conv. olefin) | | | | | | | |
| $C_4^-$, wt% | 0.94 | 4.51 | 2.17 | 0.29 | 0.53 | 0.49 | 0.29 |
| $C_5$-330F Gasoline, wt % | 91.45 | 31.98 | 25.27 | 21.35 | 19.98 | 21.45 | 26.90 |
| 330F + Distillate, wt % | 7.61 | 63.51 | 72.56 | 78.37 | 79.59 | 78.06 | 72.81 |
| GASOLINE, API | 79.4 | 73.8 | 73.8 | 73.1 | 73.3 | 73.4 | 73.0 |
| 5 wt %, F | 93 | 94 | 96 | 97 | 97 | 96 | 133 |
| 50 wt %, F | 157 | 159 | 161 | 162 | 162 | 161 | 264 |
| 95 wt %, F | 277 | 323 | 330 | 337 | 335 | 333 | 405 |
| DISTILLATE, API | 43.5 | 49.7 | 47.3 | 47.3 | 47.2 | 47.7 | 47.55 |
| 5 wt %, F | — | 318 | 321 | 320 | 323 | 319 | 326 |
| 50 wt %, F | — | 406 | 475 | 473 | 480 | 460 | 477 |
| 95 wt %, F | — | 692 | 761 | 752 | 755 | 736 | 922 |
| TLP 50% PT, F | 156 | 334 | 358 | 370 | 363 | 355 | 378 |
| WATER, wt % FEED | — | — | 0.46 | 0.43 | — | — | — |
| OXYGEN, CONV. TO WATER, WT % | — | — | 46.11 | 43.19 | — | — | — |

| *FEED COMPONENTS | Weight % |
|---|---|
| 1-Pentene | 40.8 |
| 1-Hexene | 42.2 |
| N—Hexane | 14.5 |

TABLE II-continued

| | C$_5$-C$_6$ OLEFIN FEEDSTOCK* WITH 2.5 WT % OXYGENATES | | | | | | |
|---|---|---|---|---|---|---|---|
| DAYS ON STREAM | 1 | 2 | 3 | 4 | 5 | 6 | 7 |
| Acetaldehyde | 0.3 | | | | | | |
| Methylethylketone | 1.6 | | | | | | |
| Ethyl Acetate | trace | | | | | | |
| 1-Butanol | 0.6 | | | | | | |

Figure 2:
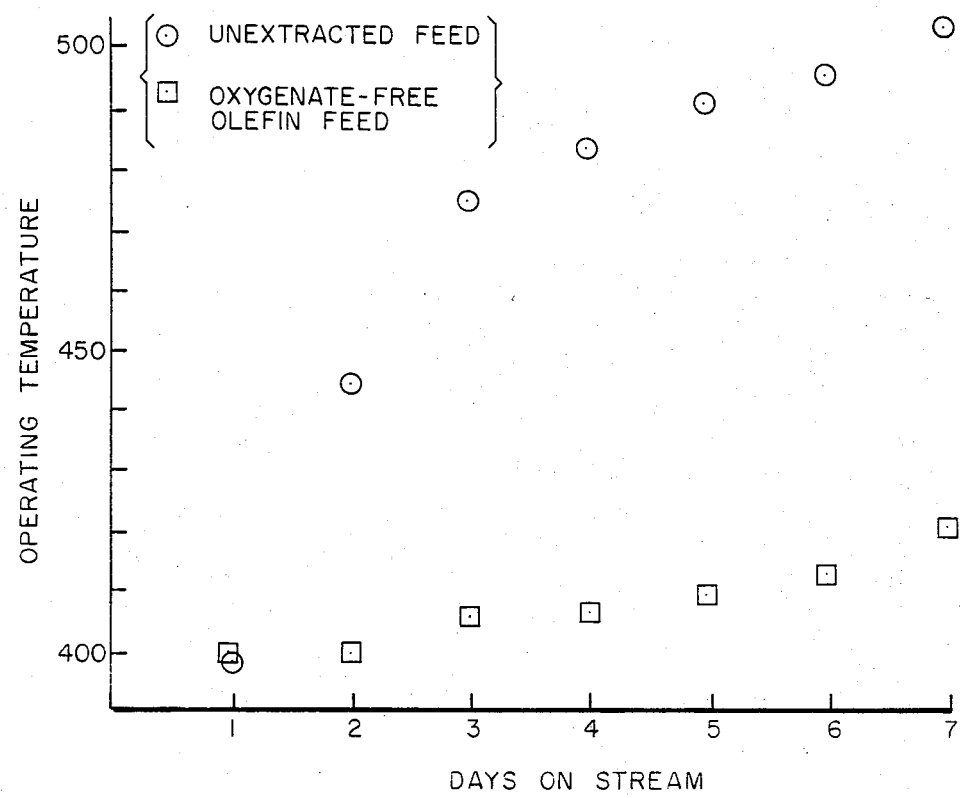

The data in Table I show a slight increase in operating temperature over the seven day run, indicating high catalyst activity. A consistently high yield of distillate product is obtained, and it is noted that the 50% boiling point for total liquid product (TLP) is also high, indicating heavy product. By contrast, the operating temperature for unextracted feed shown in Table II is increased at an average rate more than five times that of the oxygenate-free feedstock. This difference in catalyst activity is depicted in FIG. 2, which is a plot of average operating temperature vs. time on stream.

The oxygenate-containing feedstock shown in Table II can be extracted at ambient temperature with equal volumes of water. After two contact stages the acetaldehyde content is decreased to 0.01 wt % and 1-butanol to 0.03%. By employing several contact stages, a feedstock essentially free of oxygenates can be obtained. A typical Fischer-Tropsch naphtha (C$_5$-C$_6$ cut) contains trace amounts of C$_3$− aliphatics, about 0.1 to 10% C$_4$-C$_5$ aliphatics, 20–50% pentenes, 20–50% hexenes, along with substantial amounts of C$_5$+ saturates. The oxygenates may include C$_{2-4}$ aldehydes, C$_{3-6}$ aliphatic alcohols, ketones, etc., typically boiling from about 20° to 120° C.

A typical distillate mode first stage reactor system is multi-reactor system, employed with inter-zone cooling, whereby the reaction exotherm can be carefully controlled to prevent excessive temperature above the normal moderate range of about 190° to 315° (375°–600° F.). Advantageously, the maximum temperature differential across each low severity reactor is about 30° C. ($\Delta T \sim 50°$ F.) and the space velocity (LHSV based on olefin feed) is about 0.5 to 1.5. Heat exchangers provide inter-reactor cooling and reduce the effluent to flashing temperature.

Between stages it is preferred to take advantage of a significant pressure drop by flashing the effluent with a pressure differential of at least 1400 kPa (200 psi) between the first stage and phase separator vessel. By operating the first stage at elevated pressure of about 4200 to 7000 kPa (600–1000 psig), this can be achieved. Preferably, a distillate mode reactor has sufficient total pressure to assure a total olefin (feedstock plus recycle) partial pressure of at least about 3300 kPa (500 psig).

The high severity second stage reactor is relatively simple, since the higher temperature conversion does not require maximum differential temperature control closer than about 65° C. ($\Delta T \sim 120°$ F.) in the approximate elevated range of 285° C. to 375° C. (550°–700° F.). The reactor bed is maintained at a moderate super atmospheric pressure of about 400 to 3000 kPa (50–400 psig) and the space velocity for ZSM-5 catalyst to convert oxygenates and light olefins should be about 0.5 to 3 (LHSV). Preferably, all of the catalyst reactor zones in the system comprise a fixed bed down flow pressurized reactor having a porous bed of ZSM-5 type catalyst particles with an acid activity of about 160 to 200.

Various modifications can be made to the system, especially in the choice of equipment and non-critical processing steps. While the invention has been described by specific examples, there is no intent to limit the inventive concept as set forth in the following claims.

What is claimed is:

1. A process for converting olefins to heavier liquid hydrocarbons comprising
    contacting an olefinic liquid hydrocarbon feedstream containing oxygenated hydrocarbons with a polar solvent under liquid extraction conditions and recovering a polar extract phase containing the oxygenated hydrocarbons and an olefinic liquid raffinate stream substantially free of oxygenated hydrocarbons;
    contacting the olefinic liquid stream in a first catalyst reactor zone with oligomerization catalyst at elevated pressure and moderate temperature under conditions favorable for conversion of olefins to a first reactor effluent stream rich in distillate range hydrocarbons;
    flashing the distillate-rich stream and separating the first reactor effluent stream into a liquid product stream rich in distillate and a vapor stream containing lower hydrocarbons;
    separating oxygenated hydrocarbons from the polar extract phase; and
    contacting at least a portion of the vapor stream from the flashing step and recovered oxygenated hydrocarbons in a second catalyst reactor zone with oligomerization catalyst at moderate pressure and elevated temperature under conditions favorable for conversion of lower olefins and oxygenates to a second reactor effluent stream rich in heavier hydrocarbons.

2. The process of claim 1 wherein the olefinic feedstream is rich in C$_3$+ mono-olefins and contains a minor amount of C$_2$-C$_6$ oxygenates, and wherein the polar soluent consists essentially of water.

3. The process of claim 1 wherein byproduct water is recovered from at least one reactor zone and recycled as extraction solvent.

4. The process of claim 1 wherein the first and second effluent streams are fractionated to provide a gasoline-range hydrocarbon stream, and at least a portion of the gasoline stream is recycled to the first reactor zone.

5. The process of claim 4 wherein effluent is fractionated to provide a C$_3$-C$_4$ rich stream for recycle to the second reactor zone.

6. The process of claim 5 wherein at least a portion of the first effluent flashed vapor stream is partially condensed to provide a pressurized liquid for recycle to the first reactor zone.

7. The process of claim 1 wherein the first and second reactor zones contain an acid ZSM-5 type catalyst.

8. The process of claim 7 wherein the catalyst reactor zones comprise a fixed bed down flow pressurized reactor having a porous bed of ZSM-5 type catalyst particles with an acid activity of about 160 to 200.

9. The process of claim 1 wherein the first reactor zone is maintained at a pressure of about 4200 to 7000 kPa and a temperature of about 190° C. to 315° C.; and wherein the second reactor zone is maintained at a presure of about 400 to 3000 kPa and a temperature of about 285° C. to 375° C.

10. In the process for oligomerizing olefinic Fischer-Tropsch liquids to produce heavier hydrocarbons by converting olefinic feedstock containing oxygenated hydrocarbons over an acidic zeolite catalyst, the improvement which comprises:

extracting oxygenates from the feedstock;

converting the extracted feedstock in a primary stage distillate mode catalytic reactor system under low severity conditions at high pressure and moderate pressure; and recovering the oxygenates and light hydrocarbons from the primary stage for conversion in a secondary stage reactor system under high severity conditions at substantially higher temperature than the primary stage, thereby converting oxygenates and light hydrocarbons to heavier hydrocarbons.

* * * * *